(12) United States Patent
Sakamoto (10) Patent No.: US 11,202,522 B2
(45) Date of Patent: Dec. 21, 2021

(54) SUSPENSION PILLOW (71) Applicant: Hiromi Sakamoto, Yokohama (JP)

(72) Inventor: Hiromi Sakamoto, Yokohama (JP)

( * ) Notice: Subject to any disclaimer, the term of this patent is extended or adjusted under 35 U.S.C. 154(b) by 268 days.

(21) Appl. No.: 16/078,166

(22) PCT Filed: Feb. 27, 2017

(86) PCT No.: PCT/JP2017/007477
§ 371 (c)(1),
(2) Date: Aug. 21, 2018

(87) PCT Pub. No.: WO2017/150442
PCT Pub. Date: Sep. 8, 2017

(65) Prior Publication Data
US 2019/0053647 A1 Feb. 21, 2019

(30) Foreign Application Priority Data
Mar. 3, 2016 (JP) .............................. JP2016-041003

(51) Int. Cl.
*A47G 9/10* (2006.01)
*A47C 7/38* (2006.01)
(Continued)

(52) U.S. Cl.
CPC ............ *A47G 9/1009* (2013.01); *A47C 7/383* (2013.01); *A47G 9/007* (2013.01); *A47G 9/1045* (2013.01);
(Continued)

(58) Field of Classification Search
CPC .. A47G 9/1009; A47G 9/1036; A47G 9/1045; A47G 9/1054; A47G 9/1072; A47G 9/109; A47G 2200/146; A47C 21/022; A47C 21/024; A47C 7/38; A47C 7/383; A47C 7/386; A47C 16/00; A47C 9/10;
(Continued)

(56) References Cited

U.S. PATENT DOCUMENTS 1,163,945 A * 12/1915 Murdock ............... A47K 3/125
4/575.1
1,469,082 A * 9/1923 Hall ..................... B61D 33/005
297/398
(Continued)

FOREIGN PATENT DOCUMENTS

JP 3089363 10/2002
JP 2005-323633 11/2005
(Continued)

*Primary Examiner* — Peter M. Cuomo
*Assistant Examiner* — Morgan J McClure
(74) *Attorney, Agent, or Firm* — Lex IP Meister, PLLC (57) ABSTRACT

Provided is a suspension pillow that, when being used, gives an improved sense of stability and reduces a load applied on a neck and shoulders. A suspension pillow 10 is provided with: a placement part 1; a pair of support parts 3 which stand at a prescribed interval from the placement part 1; a side frame 4 which is disposed between the pair of support parts 3; and a sheet-like pillow part 5, wherein the pillow part 5 is connected, at at least three points or continuously, to the pair of support parts 3 and the side frame 4, and the pillow part 5 is connected, at a position above the pair of support parts 3, to the side frame 4.

8 Claims, 10 Drawing Sheets

(51) Int. Cl.
*A47G 9/00* (2006.01)
*A61F 5/56* (2006.01)

(52) U.S. Cl.
CPC ...... *A47G 9/1027* (2013.01); *A47G 2200/146* (2013.01); *A61F 5/56* (2013.01)

(58) Field of Classification Search
CPC ........... A47C 4/28; A47C 4/283; A47C 4/286; A47C 4/30; A47C 4/32; A47C 4/34; A47C 4/02; A47C 4/021; A47C 4/022; A47C 4/024; A47C 4/025; A47C 20/026; A61F 2007/0012; A61F 5/56; Y10S 297/11; A45D 44/10; A47D 13/107; A61G 13/121; A61G 7/072; A61G 7/07; A47K 3/127; A47K 3/064; A47K 3/122
See application file for complete search history.

(56) References Cited

U.S. PATENT DOCUMENTS

| | | | | | |
|---|---|---|---|---|---|
| 1,921,984 | A | * | 8/1933 | Moore | A47G 9/1045 5/636 |
| 2,056,479 | A | * | 10/1936 | Newman | B60N 2/882 297/400 |
| 2,460,308 | A | * | 2/1949 | Pribil | A47K 3/127 4/572.1 |
| 2,551,727 | A | * | 5/1951 | Costello | A47C 20/026 5/638 |
| 2,581,802 | A | * | 1/1952 | Lyons | A47G 9/1009 5/643 |
| 2,634,435 | A | * | 4/1953 | Budd | A47G 9/1009 132/333 |
| 2,695,415 | A | * | 11/1954 | Holton | A47D 15/003 5/655 |
| 4,063,318 | A | * | 12/1977 | Nicholson | A47G 9/1045 5/656 |
| 4,544,203 | A | * | 10/1985 | Younger | A47G 9/1009 108/118 |
| 5,033,138 | A | * | 7/1991 | Hong | A47G 9/1009 5/636 |
| 5,337,429 | A | * | 8/1994 | Tucker | A45D 19/04 4/516 |
| 5,360,258 | A | * | 11/1994 | Alivizatos | A47D 13/107 297/184.13 |
| 6,581,226 | B1 | * | 6/2003 | Brustein | A47G 9/1009 5/636 |
| 6,694,551 | B1 | * | 2/2004 | Garrido | A47C 20/026 5/638 |
| 6,839,927 | B1 | | 1/2005 | Crane | |
| 7,673,356 | B1 | * | 3/2010 | Conyers | A45D 44/10 5/643 |
| 9,398,992 | B1 | * | 7/2016 | Jansen | A61G 13/009 |
| 2003/0222484 | A1 | * | 12/2003 | Gette | A47C 7/66 297/16.2 |
| 2009/0113634 | A1 | * | 5/2009 | Macedo | A47C 21/024 5/636 |
| 2010/0001556 | A1 | * | 1/2010 | Fritsch | A47G 9/1009 297/118 |
| 2014/0201918 | A1 | * | 7/2014 | Ordonez | A47G 9/1009 5/643 |
| 2018/0184821 | A1 | * | 7/2018 | Rager | A47G 9/1009 |

FOREIGN PATENT DOCUMENTS

| | | |
|---|---|---|
| JP | 3131690 | 5/2007 |
| JP | 2008-229247 | 10/2008 |
| JP | 2011-56248 | 3/2011 |
| JP | 2016-165462 | 9/2016 |

* cited by examiner

SUSPENSION PILLOW

CROSS-REFERENCE TO RELATED APPLICATION

The present application is a continuation of PCT Application No. PCT/JP2017/007477, filed on Feb. 27, 2017, which claims priority of Japanese Patent Application No. 2016-041003 filed on Mar. 3, 2016. The contents of this application are incorporated herein by reference in their entirety.

TECHNICAL FIELD

The present invention relates to a suspending pillow.

BACKGROUND

Although there was a suspending pillow in the past, it was a belt-like one suspending in a U shape from a pair of support portions (see, for example, Patent Document 1).

PRIOR ART DOCUMENT

Patent Document

Patent Document 1: Japanese Patent Application Publication No. 2005-323633

DISCLOSURE

Technical Problem

When the user uses a conventional suspending pillow, since the pillow portion has a belt-like structure suspending from the left and right in a U shape, the head top direction is free of move and the user's head is apt to move toward the head top direction and to fall down. Therefore, it is difficult to sustainably maintain the cervical vertebrae in a natural curvature, thereby giving a sense of tension and load around the neck and shoulders of the user.

Similarly, since the pillow portion is a belt-like structure suspending from the left and right in a U shape, the pillow portion tends to swing back and forth, and there was no sense of stability when the head was placed on the pillow. Since the neck always tries to adjust the head to keep it in a fixed position, the unexpected swing of the head gives a tension and load to the neck and shoulder of the user.

An aspect of the present invention is to provide a suspending pillow which improves the feeling of stability during use and reduces the load applied to the neck and shoulder.

SUMMARY

The present invention has been devised in view of the above-mentioned problems of the prior art.

An exemplary suspending pillow of the present invention according to claim 1 includes a support base, a pair of support portions erected from the support base with a predetermined space therebetween, a side frame installed between the pair of support portions, and a sheet-like pillow portion, wherein the pillow portion is connected to the pair of support portions and the side frame at at least three portions or in a continuous manner and the pillow portion is connected to the side frame at a location above the pair of support portions.

An exemplary suspending pillow of the present invention according to claim 2 includes a support base, a support post erected from the support base, a pair of support portions connected to the support post and disposed with a predetermined space therebetween, a side frame installed between the pair of support portions, and a sheet-like pillow portion, wherein the pillow portion is connected to the pair of support portions and the side frame at at least three portions or in a continuous manner, and the pillow portion is connected to the side frame at a location above the pair of support portions.

The pillow portion may be height adjustably connected to at least one of the support portions and the side frame.

The suspending pillow may further comprise an auxiliary portion installed along the pillow portion and of which both ends are connected to the pair of support portions.

The pillow portion may further comprise a movable partition installed on the support portions or the side frame and covering a head and a face of a user.

The pillow portion or the auxiliary portion may further comprise a storage portion capable of storing an article on a surface on which a head of a user is placed.

The suspending pillow may be able to be folded and assembled.

The support base may be removable.

According to an aspect of the present invention, it is possible to provide a suspending pillow which improves the feeling of stability during use and reduces the load applied to the neck and shoulder.

DETAILED DESCRIPTION

Hereinafter, embodiments of the present invention will be described in detail with reference to the drawings.

Figure 1:
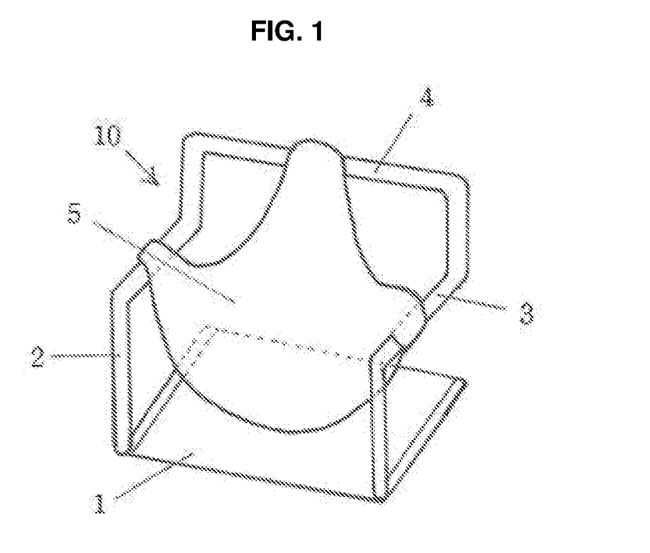
FIG. 1 is a perspective view of a suspending pillow according to a first embodiment of the present invention.

FIG. 1 shows a first embodiment of the present invention, the suspending pillow 10 includes a support base 1, support posts 2 erected from the support base 1, a pair of support portions 3 connected to the support posts 2 and disposed to have a predetermined space therebetween, a side frame 4 installed between the pair of support portions 3, and a sheet-like pillow portion 5. The pillow portion 5 is connected to the pair of support portions 3 and the side frame 4 at at least three portions or in a continuous manner. The pillow portion 5 is connected to the side frame 4 at a location above the pair of support portions 3.

Figure 2:
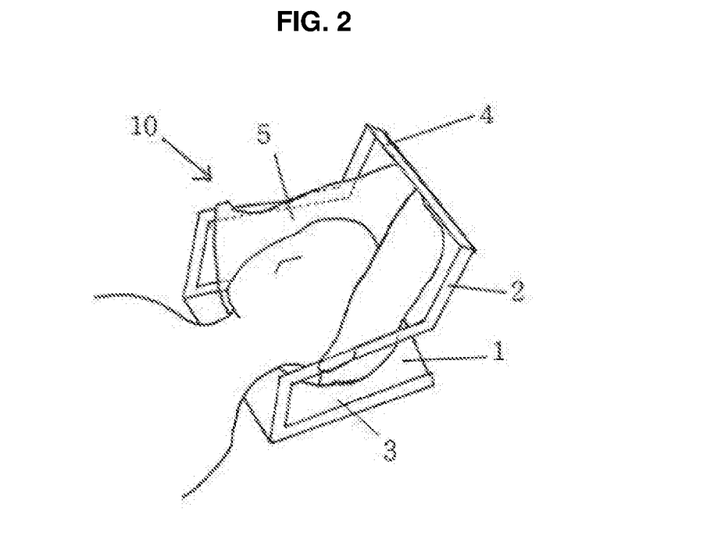
FIG. 2 is a perspective view showing a usage mode of the suspending pillow according to the first embodiment.

FIG. 2 shows a mode of use of the suspending pillow 10 of the first embodiment. When the user places his or her head on the pillow portion 5 and uses the suspending pillow 10, the pillow portion 5 supports the head instead of anti-gravitational muscle located behind the neck, thereby the load applied to the neck being reduced.

Figure 3:
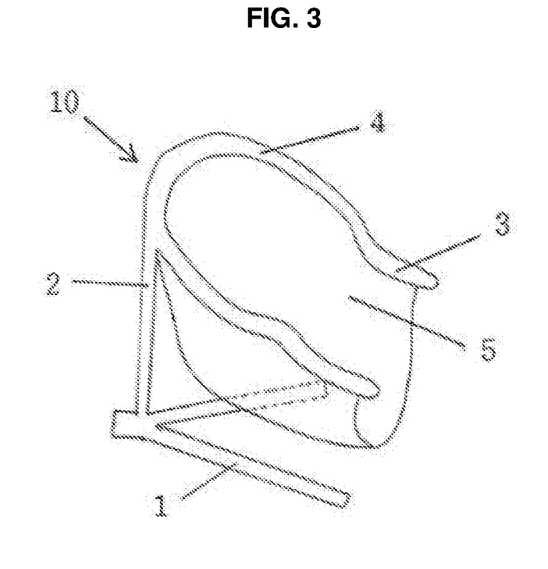
FIG. 3 is a perspective view of a modified example of the suspending pillow according to the first embodiment.

FIG. 3 shows a modified example of the suspending pillow 10 according to the present invention, the pillow portion 5 is continuously connected to the pair of support portions 3 and the side frame 4 located above the pair of support portions 3.

Figure 4:
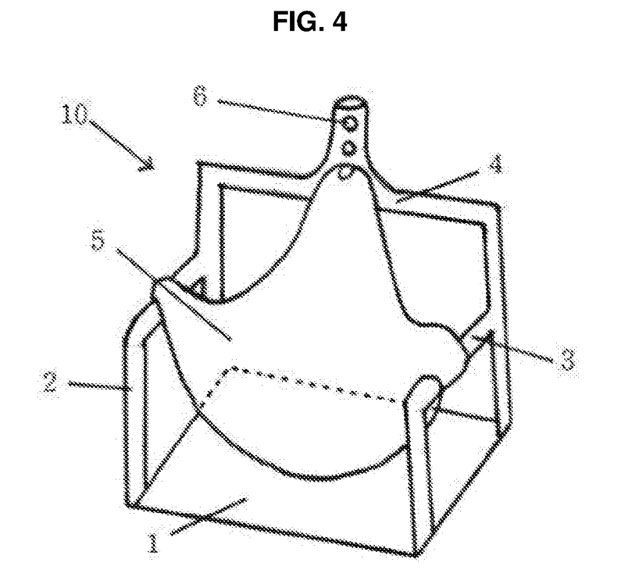
FIG. 4 is a perspective view of a suspending pillow according to a second embodiment of the present invention.

FIG. 4 shows a modified example of the suspending pillow 10 according to the present invention, but the pillow portion 5 can be connected to an arbitrary height of the side frame 4 due to a height adjuster 6. As a result, it is possible to adjust the height and inclination angle of the pillow portion 5 from 1 cm to 10 cm from the support base surface 1.

Figure 5:
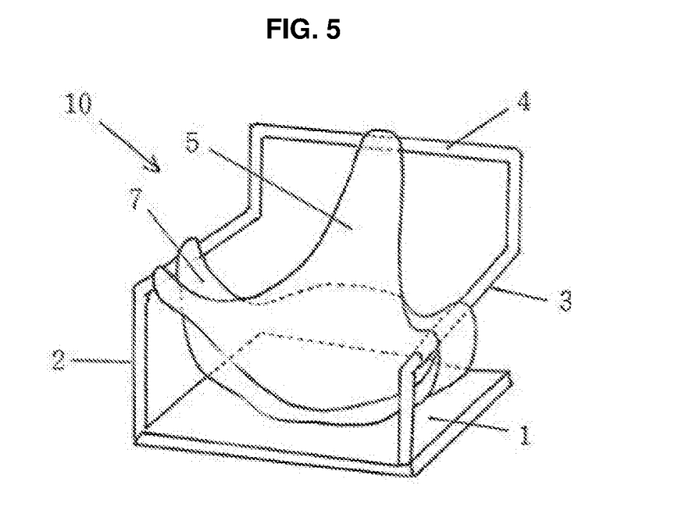
FIG. 5 is a perspective view of a suspending pillow according to a third embodiment of the present invention.

FIG. 5 shows a third embodiment of the present invention. Both ends of the pillow portion 5 are connected to the pair of support portions 3 and an auxiliary portion 7 is further provided along the pillow portion 5. The auxiliary portion 7 is placed under the pillow portion 5 and slidable in the front and back direction. Accordingly, the inclination angle and shape of the pillow portion 5 can be freely modified by adjusting the overlapping manner. Therefore, even if the size and shape of the head and the skeleton of the whole body are different, it is possible to form the shape and angle of the pillow according to the user.

The pillow portion 5 and the auxiliary portion 7 are preferably sheets such as fabrics or towel, and it is also possible to adjust the height of the pillow portion 5 on which the user's head is placed by adjusting the lengths of these pillow portions. This height adjusting may also be dealt with various fasteners including hooks and clips and various adjustors including a lace and an adhesive tape.

Figure 6:
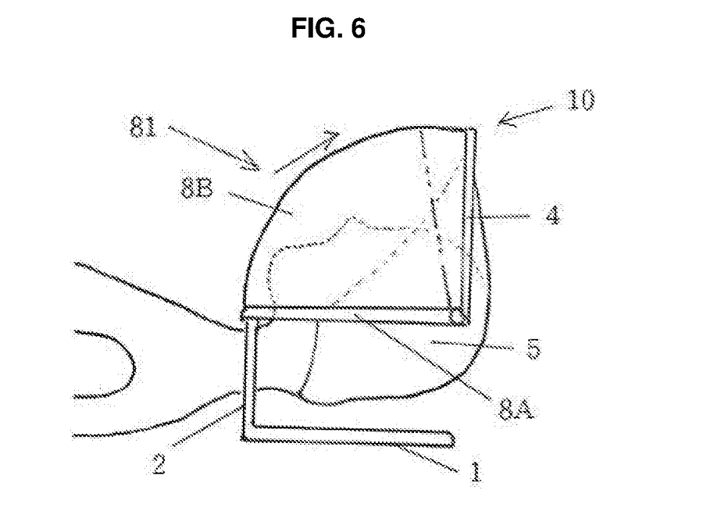
FIG. 6 is a side view showing a usage aspect of a suspending pillow according to a fourth embodiment of the present invention.

FIG. 6 shows a fourth embodiment of the present invention, which further comprises a movable partition 81 which is provided on and is detachably attached to the support posts 2 or the side frame 4 and covers the head and the face. The movable partition 81 is rotatable at the attaching position. The movable partition 81 has at least two bone parts 8A and a cover part 8B stretched between these bone parts 8A. When the partition is unnecessary, it is possible to move the covering portion 8B upward or rearward, etc., thereby downsizing. The movable partition 81 is structured so that the position of the covering portion 8B can be adjusted so as to be held in an expanded state at the time of use.

Figure 7:
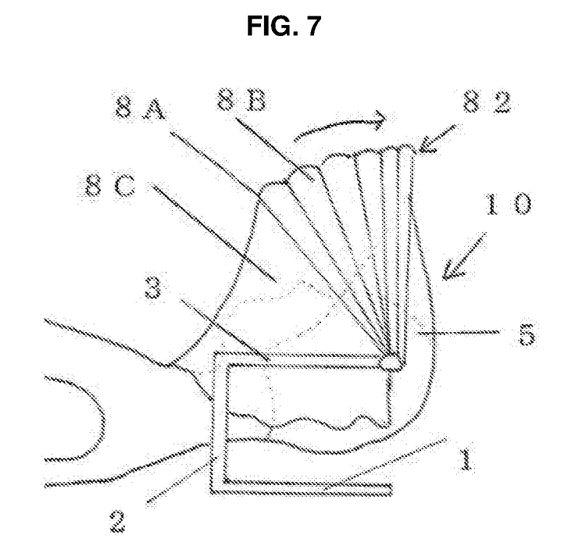
FIG. 7 is a side view showing a usage aspect of a modified example of a suspending pillow according to the fourth embodiment.

FIG. 7 shows a modification of the fourth embodiment of the present invention. The movable partition 82 covering the head and face is detachably attached to the support 2 or the side frame 4 and has at least two bone parts 8A, a covering part 8B stretched between the bone parts 8A, and a curtain portion 8C engaged with the end portion of the covering part 8B. The covering portion 8B is rotatable at the attaching position, and the curtain portion 8C can be opened and closed at the engaging portion.

As shown in FIG. 6 and FIG. 7, when the movable partitions 81 and 82 of the suspending pillow 10 are used, light such as the sun and the electric light is blocked, and the noise from the outdoors and the room is suppressed. Furthermore, it can be expected to reduce the inhalation of dust in the air, virus, pollen, etc. through the mouth and nose, protect the skin from coldness and drying in winter, and obtain mental stability as well.

Further, the shape of the movable partitions 81 and 82 is exemplary one, and there may be other movable partitions with various structures and designs, all of which are provided on the support posts 2 or the support portion 3 and are openable and closeable structures. It is preferable that when the user is placing his or her head on the pillow portion 5, the upward direction of the pillow portion 5 is opened, and after the head is placed on the pillow portion 5, the movable partition 81 or the movable partition 82 are used.

Furthermore, since the pillow portion 5 and the auxiliary portion 7 have detachably attachable structures, it is also possible to detach these and to use only the movable partition 81 or the movable partition 82 by itself.

Furthermore, by giving strength to the structure of the bone part 8A and the cover part 8B of the movable partitions 81 and 82 by using the material have hardness and pressure resistance, such as metal, wood or the like, it is possible to protect the head or face from falling things due to an earthquake or a disaster, and it may be an effective disaster prevention measure.

Figure 8:
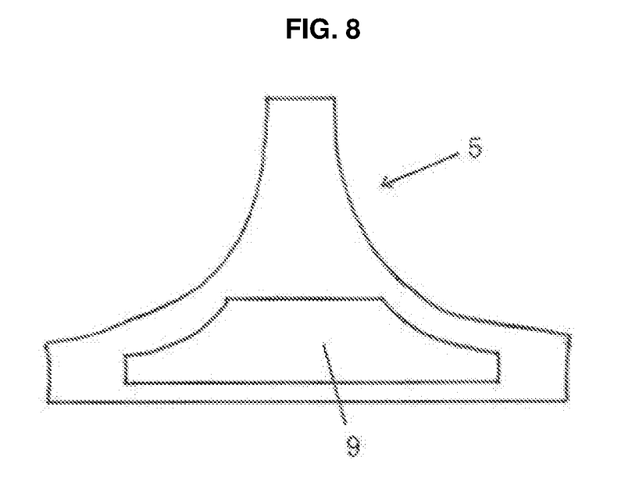
FIG. 8 is a plan view of a pillow portion according to a fifth embodiment of the present invention.

FIG. 8 shows the shape of the pillow portion according to a fifth embodiment of the present invention, and the pillow portion 5 further includes a storage portion 9 in which an article may be stored. Therefore, it is possible to store various articles such as a sheet which generates negative ions, a magnet, an acupressure tool, a cooling tool, etc.

Figure 9:
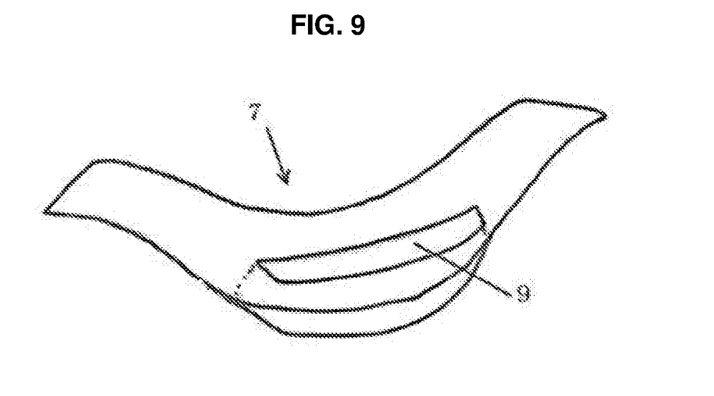
FIG. 9 is a perspective view of an auxiliary portion according to the fifth embodiment of the present invention.

FIG. 9 shows a shape of an auxiliary portion according to the fifth embodiment of the present invention, and the auxiliary portion 7 is provided with a storage portion 9 in which articles may be stored. As described above, various usages are applicable depending on the user.

In addition, since the pillow 10 has a structure in which the pillow portion 5 is disposed above the support base surface, the pillow portion 5 is prevented from contacting the ground which may be uneven due to a disaster, emergency, or using at outdoor etc., dirty or muddy, etc. Therefore, the pillow 10 may be cleanly and comfortably used.

Figure 10:
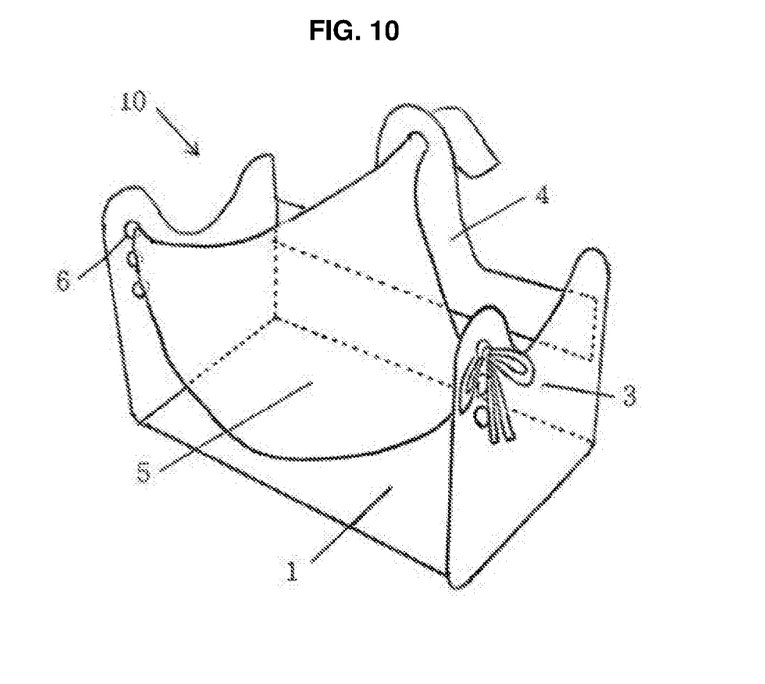
FIG. 10 is a perspective view of a suspending pillow according to a sixth embodiment of the present invention.

FIG. 10 shows a sixth embodiment of the present invention. The suspending pillow 10 includes a support base 1, a pair of support portions 3 erected from the support base 1 with a predetermined space therebetween, a side frame 4 installed between the pair of support portions 3, and a sheet-like pillow portion 5. The pillow portion 5 is connected to the support portions 2 and side frame 4 at at least three portions or in a continuous manner and is connected to the side frame 4 at a location above the pair of support portions 3.

Figure 11:
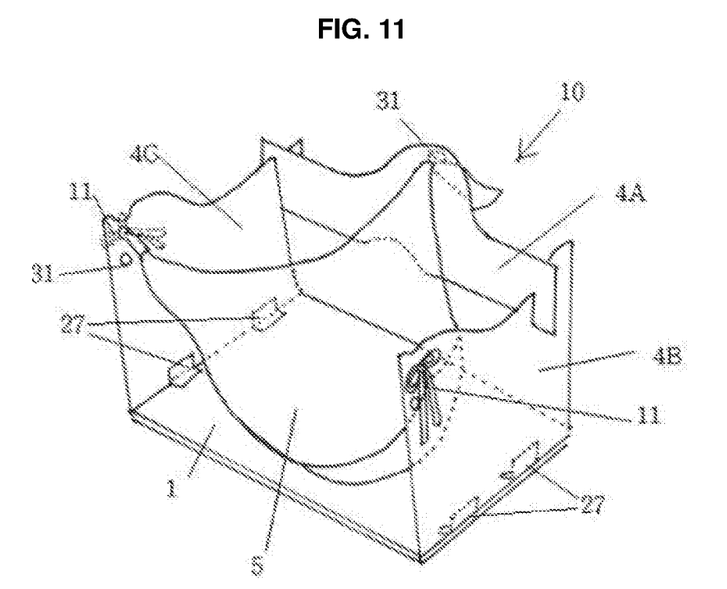
FIG. 11 is a perspective view of a suspending pillow according to a seventh embodiment of the present invention.

FIG. 11 shows a usage mode of the suspending pillow according to a seventh embodiment of the present invention, wherein the side frames 4B and 4C adjacent to the support base 1 are joined by a hinge 27, the side frame 4A is fitted on and fixed to the side frames 4B and 4C.

Figure 12:
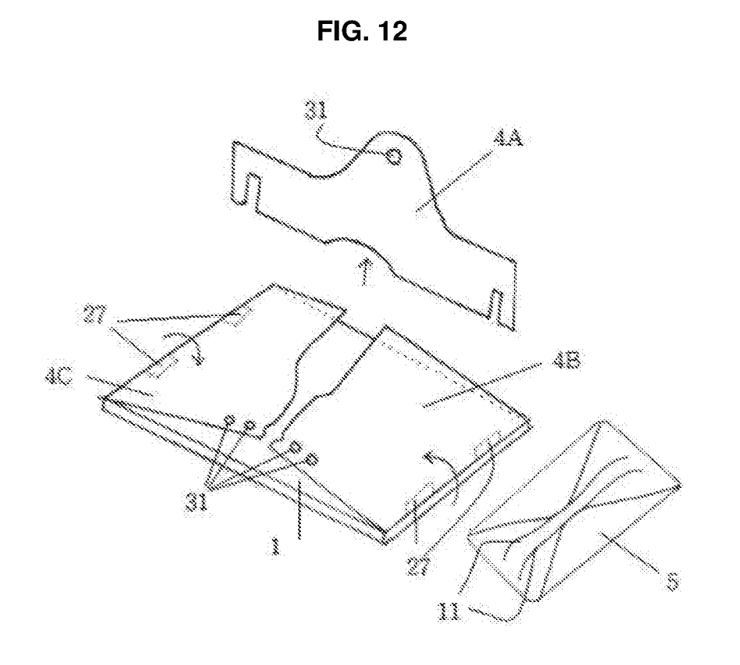
FIG. 12 is a perspective view showing a disassembled and folded state of the suspending pillow according to the seventh embodiment.

FIG. 12 shows the disassembled and folded state of the suspending pillow according to FIG. 11. The pillow portion 5 is removed and the side frame 4A which is fixed by fitting is removed from the side frames 4B and 4C. And the side frames 4B and 4C are folded inwardly with the hinge 27 to overlap the support base 1. This disassembling and folding method is merely an exemplary one, and it is also possible to combine other methods.

Figure 13:
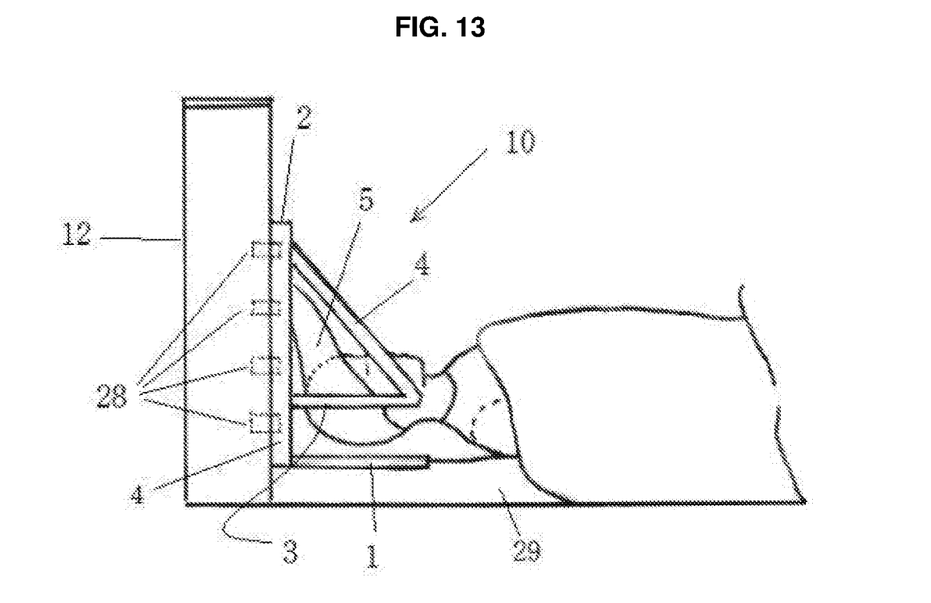
FIG. 13 is a side view showing a usage aspect of a suspending pillow according to an eighth embodiment of the present invention.

FIG. 13 shows a usage mode of the suspending pillow according to an eighth embodiment of the present invention, in which the suspending pillow 10 is attached to a bed 12. The support post 2 and the side frame 4 are attached to the bed 12 by the fasteners 28 so that the support base 1 is disposed to contact a mattress 29. The suspending pillow 10 may be detachably attached to various places such as a desk, bathtub, or medical equipment besides the bed.

Figure 14:
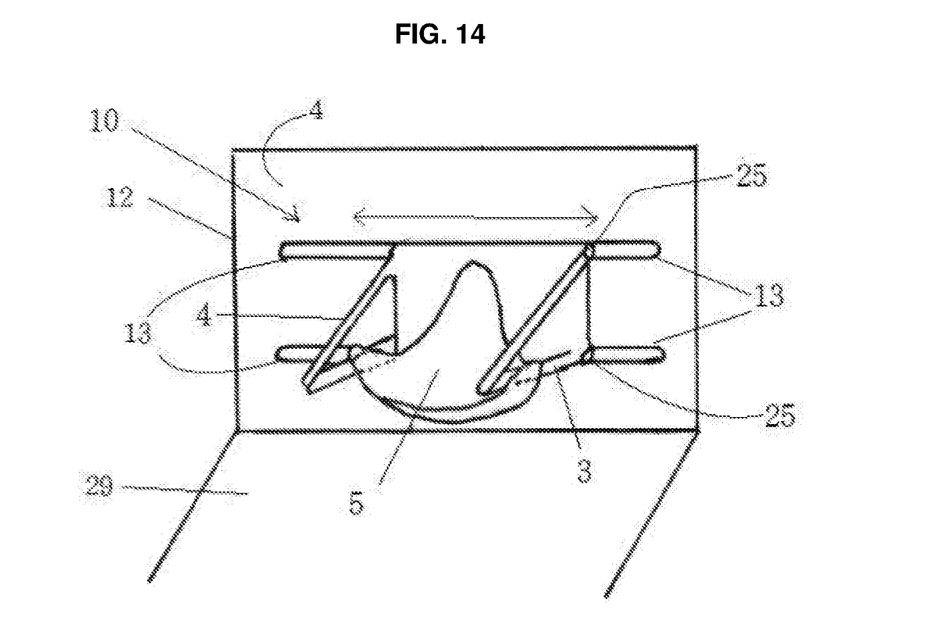
FIG. 14 is a perspective view of a suspending pillow according to a ninth embodiment of the present invention.

FIG. 14 shows a suspending pillow according to a ninth embodiment of the present invention, in which the suspending pillow 10 attached to the bed 12 as shown in FIG. 13 is arranged such that the wheels 25 mounted on the suspending pillow 10 are engaged with the rails 13 of the bed 12 and slide along the rails 13 to move right and left sides. Accordingly, the user may smoothly turn over or change posture.

Figure 15:
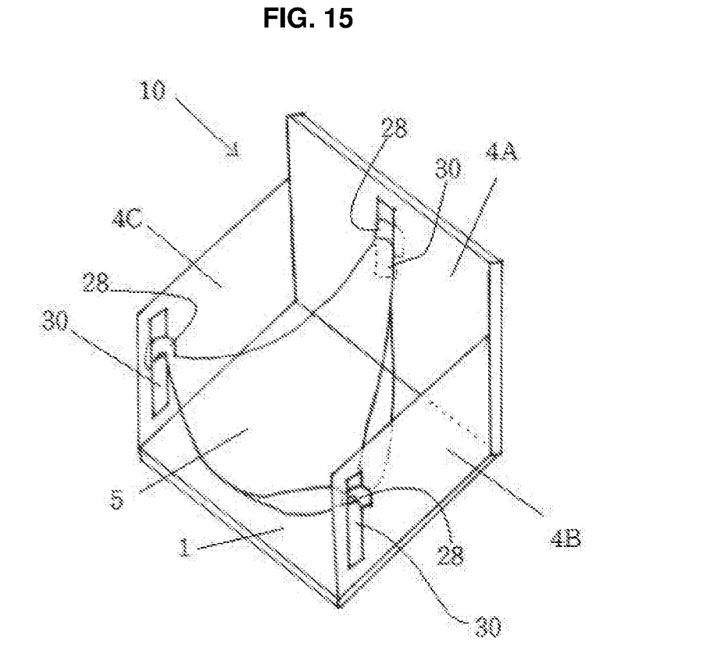
FIG. 15 is a perspective view of a suspending pillow according to a tenth embodiment of the present invention.

FIG. 15 shows a suspending pillow 10 according to a tenth embodiment of the present invention, in which the elevating parts 30 provided in the side frames 4A, 4B, 4C are electrically driven to move to a desired height. Therefore, the pillow portion 5 having the fasteners 28 hooked on the elevating parts 30 may be moved to a desired position.

Figure 16:
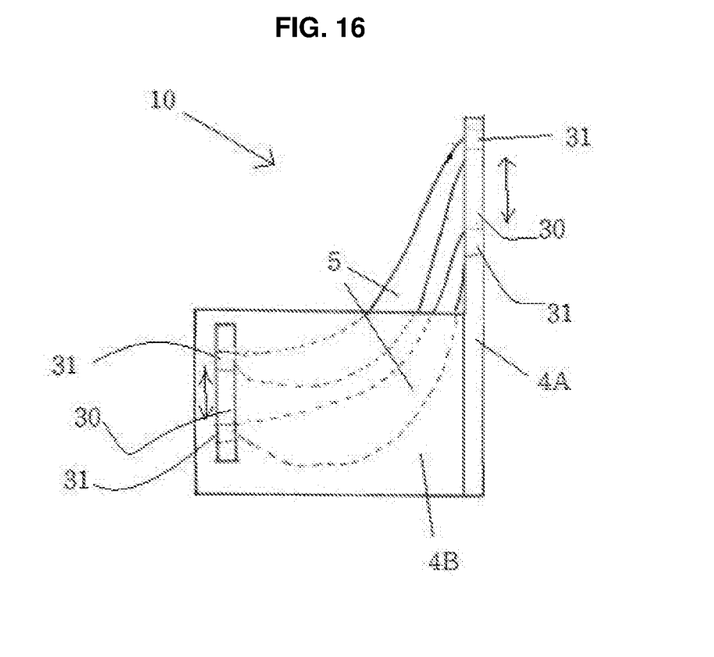
FIG. 16 is a side view of the suspending pillow according to the tenth embodiment.

FIG. 16 is a side view of FIG. 15 and shows states of the pillow portion 5 moving along the elevating parts 30. In addition to the electric motion, manual adjustment is also available. Therefore, the user may easily adjust the shape, such as height and inclination, of the pillow portion 5 with the user's head placed on the pillow portion 5.

Figure 17:
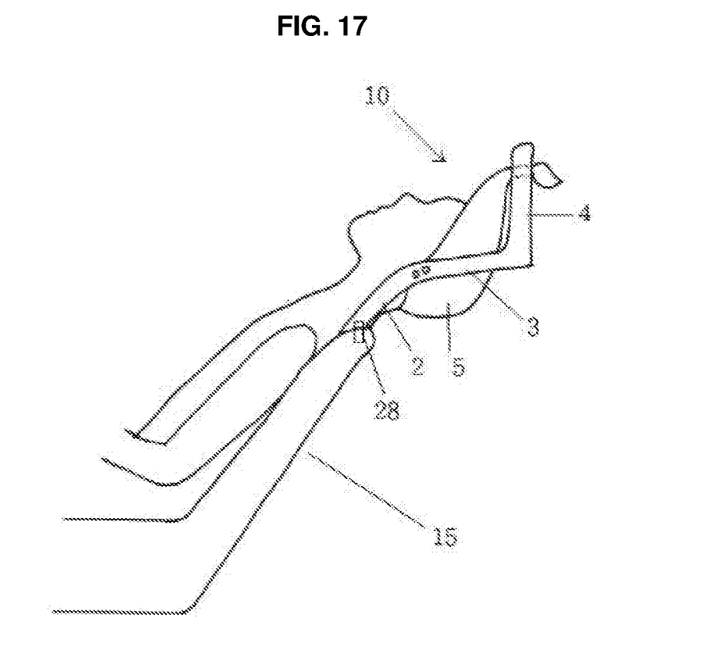
FIG. 17 is a side view showing a usage aspect of a suspending pillow according to an eleventh embodiment of the present invention.

FIG. 17 shows a usage aspect of the suspending pillow 10 according to an eleventh embodiment of the present invention in which the support post 2 is attached to the upper end of the backrest of the chair 15 with a fastener 28. The suspending pillow 10 may be used in a state that the support base 1 is removed from the support post 2 and support portion 3 or the side frame 4. As a result, the suspending pillow 10 may have a reduced weight and a compact size, so that the suspending pillow 10 may be carried and used in anywhere, such as a desk, a bathtub or a medical facility, as well as the chair.

Figure 18:
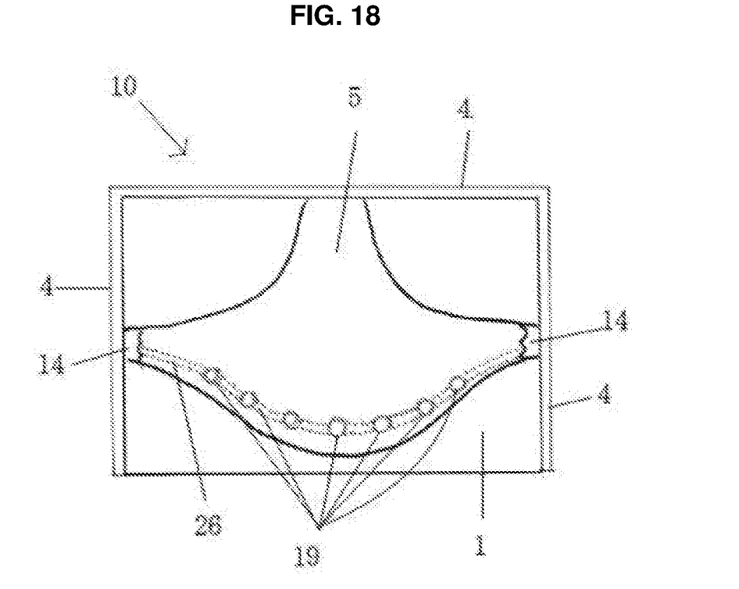
FIG. 18 is a plan view of a suspending pillow according to a twelfth embodiment of the present invention.

FIG. 18 shows a usage mode of the suspending pillow according to a twelfth embodiment of the present invention, in which an electrode pad 19 such as an electric massage or a low-frequency treatment device is provided in the pillow portion 5 and is controlled by the cable 26 and the sensor 14. Conventionally, when the electrode pad is attached to the body, time and effort are taken to wind and fix a belt on the electrode pad in order to prevent falling of the electrode pad. However, in the present embodiment, since the electrode pad 19 is provided on the pillow portion 5, there is no concern of falling, and it is possible to obtain an outstanding massage function simply by placing the head on the pillow portion 5. This embodiment may be applied to the auxiliary portion 7 besides the pillow portion 5.

Figure 19:
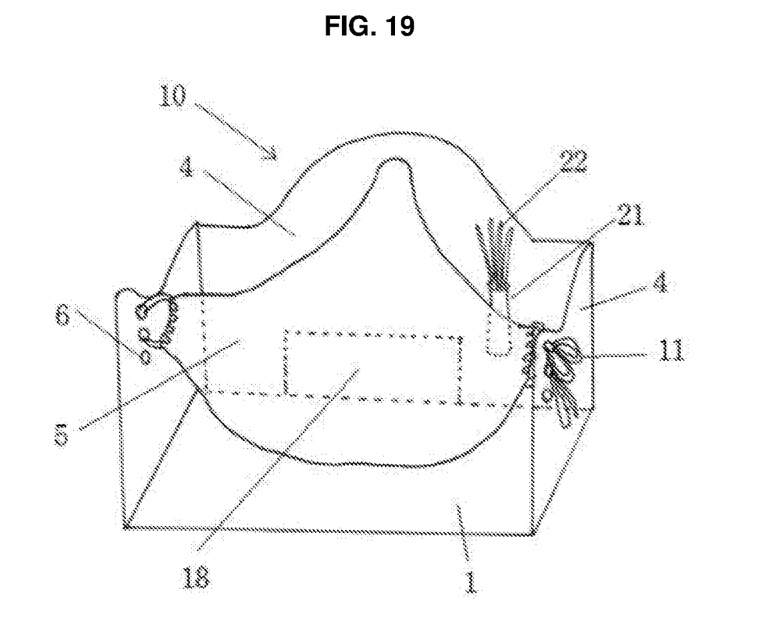
FIG. 19 is a perspective view of a suspending pillow according to a thirteenth embodiment of the present invention.

FIG. 19 shows a usage mode of the suspending pillow 10 according to a thirteenth embodiment of the present invention, in which a speaker is disposed in the side frame 4. The user placing his or her head on the pillow portion 5 may be relaxed by listening to music. Furthermore, since the fragrance containing portion 21 and the aromatic aroma 22 are provided in the side frame 4, the user may obtain a healing effect by hearing sense and olfaction.

Figure 20:
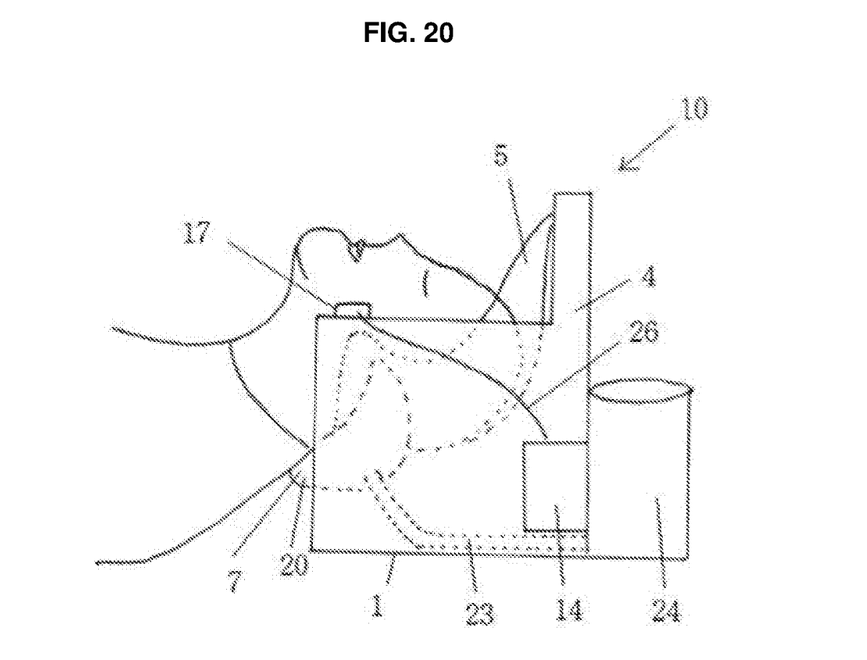
FIG. 20 is a side view of a suspending pillow according to a fourteenth embodiment of the present invention.

FIG. 20 shows a usage mode of the suspending pillow 10 according to a fourteenth embodiment of the present invention, in which the suspending pillow 10 is provided with an airbag 20, and breathing sound and snore are recorded by a microphone 17 during sleeping. The sound is sensed by a sensor 14, and when the apnea state continues, an air pump 24 delivers air through a hose 23 to expand the airbag 20. The airbag 20 pushes up the cervical vertebrae at a lower side of the occipital in a direction from down to up and holds it so as to be in a sniffing position for expanding the airway. Furthermore, when respiratory sound and snoring sound return to normal, the airbag 20 is depressurized and returns the pillow portion 5 to its original position. Accordingly, it is possible to prevent and improve the snoring and apnea syndrome.

As shown in FIG. 1 to FIG. 20, the suspending pillow 10 according to an embodiment of the present invention is characterized in that the upper end of the pillow portion 5 is connected to the pair of support portions 3 and the side frame 4 disposed above the pair of support portions 3 at at least three positions or in a continuous manner, thereby the head being stable and the load on the neck and shoulder being reduced.

It is said that a person's head has a weight of 10 to 15% of the entire boy weight, and the neck muscle is always strained and always support the head against the force of gravity. The neck muscle adjusts to keep the head in a certain position to obtain visual information, and it always works so that the neck becomes the base axis during rolling and body movements. Blood vessels supplying blood to the brain pass through the neck and important organs such as lymph, cerebrospinal fluid, and nerve are gathered in the neck, then if the cervical spine cannot be kept in a normal position due to bad posture or etc. it has been reported that the muscles of the neck are solidified abnormally, the blood circulation is declined, and a sympathetic abnormality occurs. Especially, many of people suffering mental problem such as depression complain about neck stiffness and stiff shoulders.

According to the suspending pillow 10 of the present invention, since the head is wrapped in a large area with the sheet-like pillow portion 5 and is supported in the air, the weight of the head is dispersed in various directions by the tension of the seat, so the muscles of the neck portion are released. Furthermore, if the user does gymnastics, lightly moving the whole body, in that state, the pillow part 5 and the auxiliary part 7 gently sway following the movement of the body and the muscular rigidity from the neck to the whole body is relaxed, the range of motion of the joint can be expanded without difficulty. Then, the distortion of the whole body is improved by gymnastics of a few minutes, and it is possible to correct bad posture.

Before and after light gymnastics with the head placed on the suspending pillow 10 according to the present invention, the change in posture was examined. Before gymnastics using the suspending pillow 10, the center of gravity was at the front, and therefore the shoulder came out in the forward direction and the back was rounded. In order to cover it, the waist and neck were burdened and thereby being in a state of stiffness. However, after 8 minutes of gymnastics, the center of gravity was at the center and the positions of the shoulder and head were above the midline. Therefore, the burden on the waist and neck was released and the posture was clearly improved.

Also, before and after 8 minutes of gymnastics as above, the change in the muscle hardness of the shoulder showing the degree of shoulder stiffness was examined. Before the gymnastics using the suspending pillow 10, the muscle hardness of the shoulder was 40.0 tone, whereas after gymnastics it reached 34.0 tone, a change of 6 tone appeared, it became clear that the stiff shoulder was improved.

Furthermore, before and after 8 minutes of gymnastics as above, the changes in the blood flow around the neck were examined. The blood flow rate was 9.61 ml/min/100 g-tissue before gymnastics, but after gymnastics, it became 10.59 ml/min/100 g-tissue, that is, the blood flow rate was improved by about 10%. Because blood flow in the neck directly affects the brain, improvement of blood flow is expected to prevent dementia and prevention against brain diseases.

As described above, according to the present invention, it is possible to improve the shoulder stiffness and correct the posture by performing a light gymnastic exercise while the head is placed on the suspending pillow of the present invention. It has been confirmed that the blood circulation of the neck is improved. In addition, by controlling autonomic nerves, parasympathetic nerves are made to dominate, breathing conditions are made to be stable, and a relaxed state is created in a short time. From this fact, it is expected to effectively adjust athletes' condition before athletics, prevention and improvement of apnea syndrome, sleep disorder, indefinite complaint, mental disorder, rehabilitation and the like.

It should be noted that each of the configurations of the first to sixth embodiments can be arbitrarily combined as long as those can be assembled.

LIST OF REFERENCE SIGNS 1 support base 2 support post 3 support portion 4 side frame 4A side frame A 4B side frame B 4C side frame C 5 pillow portion 6 height adjusting device 7 auxiliary portion 81 movable partition part movable partition (curtain type) 8A bone part 8B covering portion 8C curtain portion 9 storage portion 10 suspending pillow 11 lace 12 bed 13 rail 14 sensor 15 chair 16 recorder 17 microphone 18 speaker 19 electrode pad 20 air bag 21 air freshener storage portion 22 aromatic aroma 23 hose 24 air pump 25 wheel 26 cable 27 hinge 28 fastener 29 mattress 30 elevating part 31 hole

What is claimed is:

1. A suspending pillow comprising:
   a support base;
   a pair of support portions erected from the support base with a predetermined space therebetween, wherein each of the support portions has a plurality of height adjusting holes;
   a side frame installed between the pair of support portions and provided with a connection hole at a center portion of the side frame; and
   a triangular sheet pillow portion with three corners and a head rest part,
   wherein two corners of the pillow portion respectively include a string that is inserted in one of the height adjusting holes to be connected to the pair of support portions and the other corner of the pillow portion is inserted in the connection hole to be connected to the center portion of the side frame at a location above the pair of support portions.

2. The suspending pillow according to claim 1, wherein the pillow portion is height adjustably connected to at least one of the support portion and the side frame.

3. The suspending pillow according to claim 1, further comprising an auxiliary portion installed along the pillow portion and of which both ends are connected to the pair of support portions.

4. The suspending pillow according to claim 3, wherein the pillow portion or the auxiliary portion further comprise a storage portion capable of storing an article on a surface on which a head of a user is placed.

5. The suspending pillow according to claim 1, further comprising a movable partition installed on the support portions or the side frame and covering a head and a face of a user.

6. The suspending pillow according to claim 1, wherein the pillow portion further comprises a storage portion capable of storing an article on a surface on which a head of a user is placed.

7. The suspending pillow according to claim 1, wherein the suspending pillow is able to be folded and assembled.

8. The suspending pillow according to claim 1, wherein the support base is removable.

* * * * *